United States Patent [19]

Gymer et al.

[11] Patent Number: 4,960,782
[45] Date of Patent: Oct. 2, 1990

[54] TRIAZOLE ANTIFUNGAL AGENTS

[75] Inventors: Geoffrey E. Gymer, Sandwich; Kenneth Richardson, Birchington, both of England

[73] Assignee: Pfizer Inc., New York, N.Y.

[21] Appl. No.: 425,890

[22] Filed: Oct. 23, 1989

Related U.S. Application Data

[63] Continuation of Ser. No. 99,927, Sep. 23, 1987, abandoned, which is a continuation-in-part of Ser. No. 797,200, Nov. 14, 1985, abandoned, which is a continuation of Ser. No. 576,517, Feb. 2, 1984, abandoned.

[30] Foreign Application Priority Data

Feb. 25, 1983 [GB] United Kingdom ............... 8305377

[51] Int. Cl.$^5$ .................. A61K 31/41; A01N 43/653; C07D 249/08
[52] U.S. Cl. ................................... 514/383; 548/266.6
[58] Field of Search ....................... 548/266.6; 514/383

[56] References Cited

U.S. PATENT DOCUMENTS

| | | | |
|---|---|---|---|
| 4,359,470 | 11/1982 | Kramer et al. | 548/262 |
| 4,382,944 | 5/1983 | Kramer et al. | 548/262 |
| 4,404,216 | 9/1983 | Richardson | 514/383 |
| 4,416,682 | 11/1983 | Worthington | 548/262 |
| 4,428,949 | 1/1984 | Kramer et al. | 548/101 |
| 4,495,191 | 1/1985 | Ehrhardt et al. | 548/262 |
| 4,510,148 | 4/1985 | Richardson et al. | 514/383 |
| 4,518,604 | 5/1985 | Richardson et al. | 548/262 |

FOREIGN PATENT DOCUMENTS 2078719A 1/1982 United Kingdom .

OTHER PUBLICATIONS

Burger, Medicinal Chemistry, 2nd Ed. (N.Y., 1960), p. 1055 (RS 403B8).

Primary Examiner—Richard L. Raymond
Assistant Examiner—Patricia L. Morris
Attorney, Agent, or Firm—Peter C. Richardson; J. Trevor Lumb; James M. McManus

[57] ABSTRACT

Triazoles of the formula

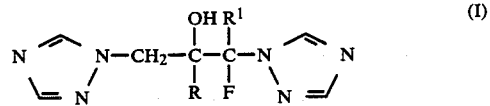

where R is phenyl optionally substituted by 1 to 3 substituents each independently selected from F, Cl, Br, I, $CF_3$, $C_1$-$C_4$ alkyl and $C_1$-$C_4$ alkoxy, or R is 5-chloropyrid-2-yl; and $R^1$ is H, $CH_3$ or F; and their pharmaceutically and agriculturally acceptable salts. The compounds are useful as human and agricultural fungicides.

5 Claims, No Drawings

TRIAZOLE ANTIFUNGAL AGENTS

CROSS-REFERENCE TO RELATED APPLICATIONS

This application is a continuation application of copending application Ser. No. 99,927, filed Sept. 23, 1987 which is a continuation-in-part of pending U.S. application Ser. No. 797,200, filed Nov. 14, 1985, now abandoned, which in turn is a continuation of U.S. application Ser. No. 576,517, filed Feb. 2, 1984, now abandoned.

BACKGROUND OF THE INVENTION

This invention relates to novel bis-triazole derivatives which have antifungal activity and are useful in the treatment of fungal infections in animals, including humans, and as agricultural fungicides.

British patent application No. 2,078,719A, published Jan. 13, 1982 and European patent application No. 44,605, published Jan. 27, 1982 (both assigned to Imperial Chemical Industries Limited) disclose compounds of the general formula:

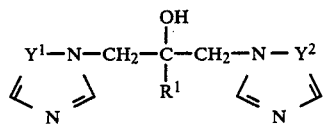

where $R^1$ is an optionally-substituted alkyl, cycloalkyl (e.g., cyclopentyl or cyclohexyl), aryl (e.g., phenyl or 2,4-dichlorophenyl) or aralkyl (e.g., benzyl) group, and $Y^1$ and $Y^2$ are $=CH$ or $=N-$; and salts or metal complexes and ethers or esters thereof. These compounds are stated to be useful as fungicides as plant growth regulants. They are also stated to be active against the fungus diseases of humans. Among the compounds specifically disclosed therein are such bis-triazole derivatives as 2-(2,4-dichlorophenyl)-1,3-bis(1H-1,2,4-triazol-1-yl)propan-2-ol and its corresponding 2- and 4-chlorophenyl analogs. The corresponding 3-chlorophenyl and 4-bromophenyl compounds are also embraced by the statement of invention. However, these particular compounds have now been found to be teratogenic, which severely limits their use in treating human mycoses.

U.S. Pat. No. 4,404,216, issued Sept. 13, 1983 is directed to the single antifungal compound 2-(2,4-difluorophenyl)-1,3-bis(1H-1,2,4-triazol-1-yl)propan-2-ol, a compound having the above formula but wherein $R^1$ is 2,4-difluorophenyl.

Since the 1960's an increase in fungal infections, particularly those caused by Candida and Aspergillus species, has been reported among immunocompromised patients. While any Aspergillus species can be the responsible cause of aspergillosis, *A. fumigatus* is the most prevalent cause, followed closely by *A. flavus*. The availability of agents effective against such opportunistic pathogens is, therefore, highly desirable.

SUMMARY OF THE INVENTION

According to the invention, there are provided compounds of the formula:

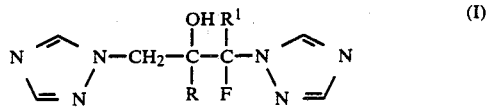

where R is phenyl optionally substituted by 1 to 3 substituents each independently selected from F, Cl, Br, I, $CF_3$, $C_1$–$C_4$ alkyl and $C_1$–$C_4$ alkoxy, or R is 5-chloropyrid-2-yl; and $R^1$ is H, $CH_3$ or F; and their pharmaceutically and agriculturally acceptable salts.

$C_3$ and $C_4$ alkyl and alkoxy groups can be straight or branched chain.

The invention also provides a pharmaceutical composition comprising a compound of the formula (I) or a pharmaceutically acceptable salt thereof, together with a pharmaceutically acceptable diluent or carrier.

The invention further provides a compound of the formula (I) or a pharmaceutically acceptable salt thereof, for use in medicine, in particular for treating fungal infections in animals, including humans.

The invention yet further provides a plant or seed antifungal composition comprising a compound of the formula (I) or an agriculturally acceptable salt thereof, together with an agriculturally acceptable diluent or carrier.

The invention yet further provides a method of treating an animal (including a human being), a plant or seed having a fungal infection, which comprises treating said animal, plant or seed, or the locus of said plant, with an antifungally effective amount of a compound of the formula (I) or with, as appropriate, a pharmaceutically or agriculturally acceptable salt thereof.

When R is said optionally substituted phenyl group, it is preferably phenyl substituted by 1 to 3 substituents, more preferably 1 or 2 substituents, each independently selected from F, Cl, Br, I and $CF_3$. The preferred individual groups represented by R are 4-fluorophenyl, 4-chlorophenyl, 4-bromophenyl, 4-iodophenyl, 4-trifluoromethylphenyl, 2-chlorophenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl and 4-bromo-2,5-difluorophenyl. The more preferred groups represented by R are 2,4-difluorophenyl, 2,4-dichlorophenyl, 4-fluorophenyl and 4-chlorophenyl. The most preferred group represented by R is 2,4-difluorophenyl.

$R^1$ is preferably H or F.

In the most preferred compound, R is 2,4-difluorophenyl and $R^1$ is H.

DETAILED DESCRIPTION OF THE INVENTION

The compounds of the formula (I) can be prepared in conventional manner according to the following reaction scheme:

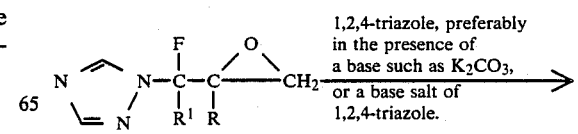

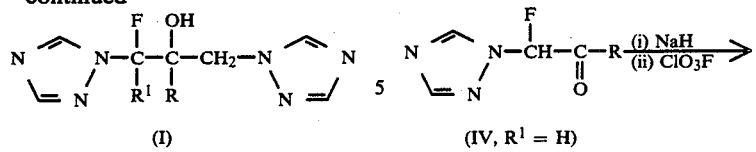

(I)

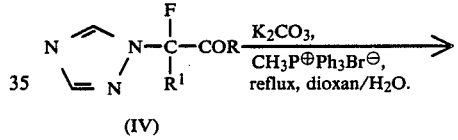

(IV, R¹ = H)

In a typical reaction, the epoxide (II), 1,2,4-triazole and anhydrous potassium carbonate are heated together at a temperature of ca. 40°–120° C. in a suitable solvent, e.g. anhydrous dimethylformamide, until the reaction is complete. The product (I) can then be isolated and purified in a conventional manner.

If a base salt of 1,2,4-triazole is used, this is preferably an alkali metal salt and, most preferably, the sodium or potassium salt.

The starting materials of the formula (II) in which R¹=H or CH₃ are obtainable conventionally, e.g.

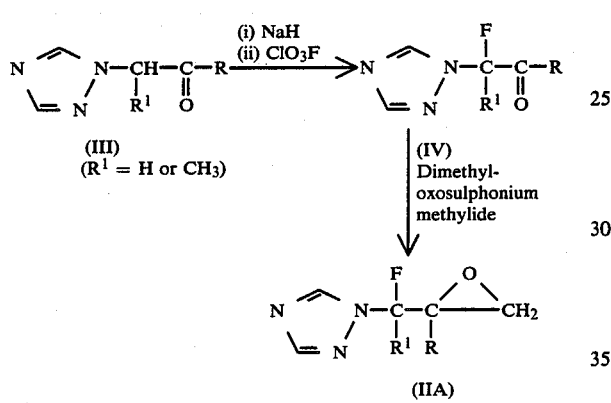

(III) (R¹ = H or CH₃)

(IV) Dimethyl-oxosulphonium methylide (IIA)

It is not essential to isolate and purify compound (IIA) and it can be converted in situ to the desired Product.

Trimethylsulphoxonium iodide and sodium hydride in dimethylsulphoxide is generally used to generate dimethyloxosulphonium methylide in situ.

The ketones (III) are either known compounds (see e.g. European patent application publication No. 0044605 or U.K. patent application publication No. 2099818A) or can be prepared by methods analogous to those of the prior art.

An alternative route to the ketones (IV) (R¹=H) is as follows:

Compound (IV).

The compounds of the formula (I) contain at least one chiral centre, and the invention includes both resolved and unresolved forms. When R¹ is H or CH₃, the compounds exist in two diastereoisomeric pairs. A typical complete separation of such a compound of the formula (I) into its two diastereoisomeric pairs is described in Example 2, and a partial separation in Example 1(B).

The starting materials of the formula (II) in which R¹=F can be prepared as follows:

(V)

Dimethyloxo-sulphonium methylide

[(CH₃)₂S=CH₂]

(IIB)

Again it is not essential to isolate the intermediate (IIB).

Another route to the oxiranes (II) in which R¹ is H, CH₃ or F is as follows:

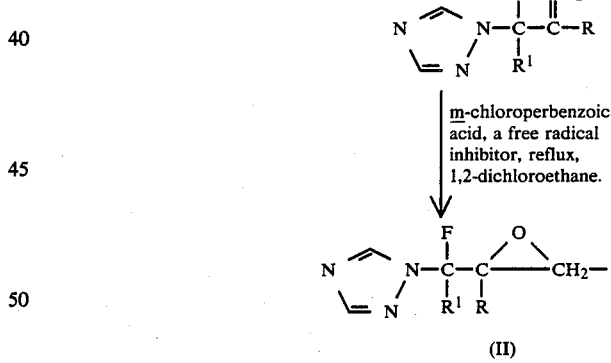

(IV)

m-chloroperbenzoic acid, a free radical inhibitor, reflux, 1,2-dichloroethane.

(II)

The preferred free radical inhibitor is 3,3'-di-t-butyl-4,4'-dihydroxy-5,5'-dimethyl-diphenylsulphide, of the formula:

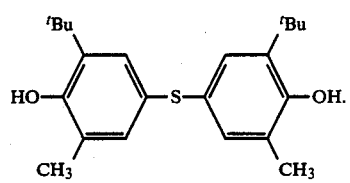

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts are obtained by conventional procedures, e.g. by mixing solutions containing approximately equimolar amounts of the free base and desired acid, and the required salt is collected by filtration, if insoluble, or by evaporation of the solvent.

The compounds of the formula (I) and their pharmaceutically acceptable salts are antifungal agents, useful in combating fungal infections in animals, including humans. For example they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus flavus, Aspergillus fumigatus,* Coccidioides, Paracoccidioides, Histoplasma or Blastomyces.

The in vitro evaluation of the antifungal activity of the compounds can be performed by determining the minimum inhibitory concentration (m.i.c.) of the test compounds in a suitable medium at which growth of the particular micro-organism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Cryptococcus neoformans, Aspergillus fumigatus,* Trichophyton spp; Microsporum spp; Epidermophyton floccosum, Coccidioides immitis and *Torulopsis glabrata.*

The in vivo evaluation of the compounds can be carried out at a series of dose levels by intraperitoneal or intravenous injection or by oral administration, to mice which are inoculated with a strain of *Candids albicans.* Activity is based on the survival of a treated group of mice after the death of an untreated group of mice following 48 hours observation. The dose level at which the compound provides 50% protection against the lethal effect of the infection (PD$_{50}$) is noted.

In tests for activity against systemic aspergillosis in mice, mice are infected with a strain of *Aspergillus flavus* by i.v. injection via the tail vein. Untreated (control) mice normally die within 5 to 10 days of infection with *A. flavus.* Each test compound is administered to a group of infected mice at an oral dose level of 20 mg./kg 1 hour and 4 hours after infection, and then twice daily for the next 4 days. The increase in mean survival time (MST) of the treated mice compared with that of a control group of mice infected with the same strain at the same time, is then determined. The MST is a measure of activity in vivo. It is a function of the pharmacological and pharmacokinetic properties of a compound as well as of its potency. MIC data affords only a measure of in vitro potency. MST data, like PD$_{50}$ data, represent a far more meaningful assessment of antifungal activity than MIC data.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerella cingulata, Penicillium digitatum, Botrytis cinerea* and *Rhizoctonia solani.*

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions can also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack.

The following Examples illustrate the invention. All temperatures are in °C.

EXAMPLE 1

Procedure (A)

1,3-Bis(1H-1,2,4-triazol-1-yl)-2-(2,4-difluorophenyl)-1-fluoropropan-2-ol (mixture of two diastereomeric pairs)

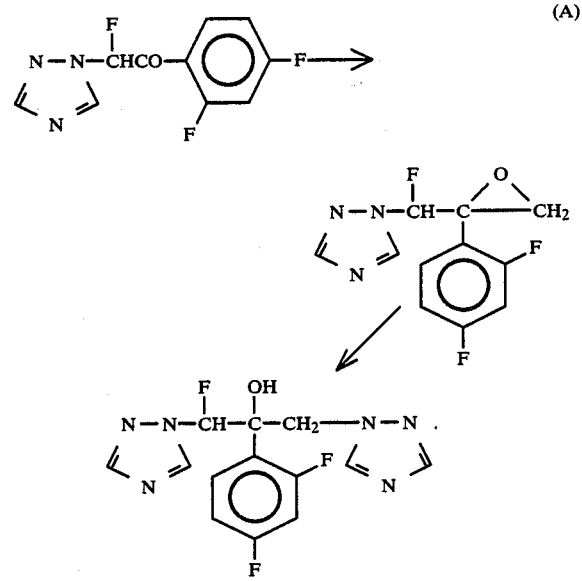

A mixture of sodium hydride (21 mg. of a 60% dispersion in oil, 0.54 mM of sodium hydride) and trimethyl sulphoxonium iodide (143 mg; 0.65 mM) was stirred under dry nitrogen and anhydrous dimethyl sulphoxide (4 ml) was added. After forty minutes anhydrous tetrahydrofuran (4 ml) was added to the solution and the mixture was cooled to −40°. A solution of 2-(1H-1,2,4-triazol-1-yl)-2,2′,4′-trifluoroacetophenone (130 mg; 0.54 mM) in tetrahydrofuran (3 ml) was added and the temperature was allowed to rise slowly to room temperature. Water (10 ml) and ether (50 ml) were then added. The ethereal layer was separated, dried over magnesium sulphate and evaporated to yield the intermediate epoxide (A) as a gum. To this were added 1,2,4-triazole (112 mg; 1.62 mM), anhydrous potassium carbonate (223 mg; 1.62 mM) and anhydrous dimethylformamide (4 ml) and the mixture was stirred and heated at 70 for 2 hours. The mixture was cooled, water (50 ml) was added and the mixture was extracted with methylene chloride (2×50 ml). Co-evaporation of the combined methylene chloride extracts with xylane yielded a gum which contained the crude product as a mixture of 2 diastereomeric pairs. The gum was chromatographed on a column of silica eluting with a mixture of 4% (by volume) methanol in methylene chloride. Collection of the product-containing fractions followed by evaporation gave the title compound as a colourless solid (72 mg; 41%) which, after crystallisation from a mixture of ethyl acetate and cyclohexane, had a melting point of 142°–145°. The compound was a mixture of two diastereoisomeric pairs in a ratio of approximately 4:1.

| Analysis % | |
|---|---|
| Found: | C,48.3; H,3.5; N,25.6; |
| Required for $C_{13}H_{11}F_3N_6O$: | C,48.2; H,3.4; N,25.9. |

Procedure (B)

Partial resolution of the two diastereoisomeric pairs of 1,3-bis(1H-1,2,4-triazol-1-yl)-2-(2,4-difluorophenyl)-1-fluoropropan-2-ol A mixture of sodium hydride (406 mg. of a 60% dispersion in oil, 10.17 mM of sodium hydride) and trimethylsulphoxonium iodide (2.68 gm, 12.20 mM) was stirred under dry nitrogen and anhydrous dimethyl sulphoxide (40 ml.) was added. After 30 minutes anhydrous tetrahydrofuran (40 ml.) was added to the solution and the mixture cooled to −30°. A solution of 2-(1H-1,2,4-triazol-1-yl)-2,2′,4′-trifluoroacetophenone (2.45 g; 10.17 mM) in tetrahydrofuran (30 ml.) was added and the temperature was allowed to rise slowly to 0°. Water (50 ml.) was added and the mixture was extracted with three aliquots (60 ml.) of ether. The combined ethereal layers were dried over MgSO4 and evaporated to yield the intermediate epoxide (A) (1.89 g.) as a semi-crystalline solid. To this were added 1,2,4-triazole (3.51 g; 50.85 mM), anhydrous potassium carbonate (7.0 g; 50.85 mM) and anhydrous dimethylformamide (40 ml.) and the mixture was stirred and heated at 70° for 18 hours. The mixture was cooled, water (100 ml.) added and the mixture was extracted with methylene chloride (3×60 ml.). Co-evaporation of the combined methylene chloride extracts with xylene, after drying over MgSO4, yielded a gum. This gum was chromatographed on a column of silica eluting with a mixture of 3% (by volume) methanol in methylene chloride followed by 4% methanol in methylene chloride. The two diastereoisomeric pairs were eluted pure in unresolved form. Collection and evaporation of the Product-containing fractions gave the title compound as a colourless solid (1.1 g) (33%). High pressure liquid chromatography (HPLC) showed the product to be a mixture of two diastereomeric pairs in a ratio of approximately 4:1.

Crystallisation of this isomeric mixture from a mixture of ethyl acetate (20 ml) and hexane (30 ml) gave pure diastereoisomeric pair 1 as a colourless crystalline solid, (688 mg.), m.p. 149°–150°.

| Analysis % | |
|---|---|
| Required for $C_{13}H_{11}F_3N_6O$: | C,48.2; H,3.4; N,25.9; |
| Found: | C,48.0; H,3.4; N,25.9. |

Concentration of the crystallisation liquors gave a second crop of crystals (88 mg.), m.p. 117°–123°. H.P.L.C. showed this to be a mixture of the two diastereomeric pairs in a ratio of approximately 1:5.

| Analysis % | |
|---|---|
| Required for $C_{13}H_{11}F_3N_6O$: | C,48.2; H,3.4; N,25.9; |
| Found: | C,48.0; H,3.5; N,26.0. |

Evaporation of the final crystallisation liquors yielded a gum (170 mg), shown by H.P.L.C. to contain the two diastereomeric Pairs in a ratio of approximately 1:1.

EXAMPLE 2

Complete separation of the two diastereoisomeric pairs of 1,3-Bis(1H-1,2,4-triszol-1-yl)-2-(2,4-difluorophenyl)-1-fluoropropan-2-ol 1,3-Bis(1H-1,2,4-triazol-1-yl)-2-(2,4-difluorophenyl)-1-fluoropropan-2-ol (170 mg., as the approximately 1:1 mixture of the diastereomeric pairs from Example 1 Procedure (B)) was dissolved in methylene chloride (1 ml) and then absorbed onto a column (2×30 cm) of Merck (Trademark) silica (230–400 mesh) prepared in a mixture of hexane/isopropanol/acetic acid (60/40/2). Elution with 500 ml. of the same solvent under moderate pressure (5 p.s.i.) gave complete separation of the diastereoisomeric pairs. Evaporation of the solvent gave the isomers as colourless solids (ethyl acetate was successfully used as the eluent in a repeat of this procedure).

Diastereoisomeric pair 1 (eluted first): 80 mg. crystallisation from ethyl acetate/hexane gave a crystalline solid, m.p. 148°–150°.

| Analysis % | |
|---|---|
| Required for $C_{13}H_{11}F_3N_6O$: | C,48.2; H,3.4; N,25.9; |
| Found: | C,48.0; H,3.4; N,25.9. |

Diastereoisomeric pair 2: 70 mg. crystallisation from ethyl acetate/hexane gave a crystalline solid, m.p. 137°–139°.

| Analysis % | |
|---|---|
| Required for $C_{13}H_{11}F_3N_6O$: | C,48.2; H,3.4; N,25.9; |
| Found: | C,48.4; H,3.5; N,25.7. |

EXAMPLES 3–6

The following compounds were prepared similarly to the method of Example 1 procedure (A) from appropriate starting materials, using in the chromatography, methylene chloride containing, by volume, 2% isopropyl alcohol and 0.2% ammonia (S.G. 0.880), and crystallising the products from ethyl acetate/petroleum ether (b.p. 60°–80°):

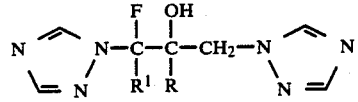

| Example No. | R | $R^1$ | m.p. (°C.) | Analysis % (Theoretical in brackets) | | |
|---|---|---|---|---|---|---|
| | | | | C | H | N |
| 3 | 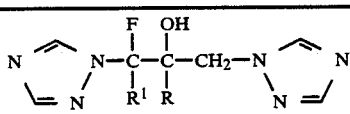 | H | 134–6 | 48.3 (48.4 | 3.7 3.7 | 25.8 26.0) |
| 4 | (4-F-phenyl) | H | 74–6 | 50.6 (50.9 | 4.1 3.9 | 26.7 27.4) |
| 5 | (2,4-diCl-phenyl) | H | (a) 200–202 | 43.7 (43.7 | 3.1 3.1 | 22.9 23.5) |
| | | | (b) 180–4 [see below] | 44.1 (43.7 | 3.2 3.1 | 23.4 23.5) |
| 6 | (2-F,4-F-phenyl) | $CH_3$ | 138–145 | 49.2 (49.6 | 3.8 3.9 | 24.6 24.8) |

In Examples 3, 4 and 6, no separation of the diastereomers was achieved. In Example 5, the chromatography resulted in a partial separation. One pure diastereomer, called "(a)", was eluted first, and was crystallised from ethyl acetate/petroleum ether (b.p. 60°–80°), m.p. 200°–202°. After this, a mixture of the diastereomers in a ratio of about 1:1 was eluted, called "(b)", and was crystallised from ethyl acetate/petroleum ether (b.p. 60°–80°), m.p. 180°–184°.

EXAMPLE 7

(i) 2-(1H-1,2,4-Triazol-1-yl)-2,2,2',4'-tetrafluoroacetophenone

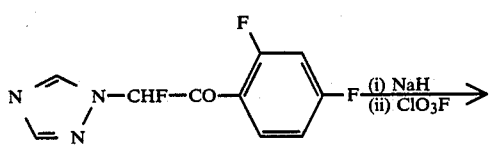

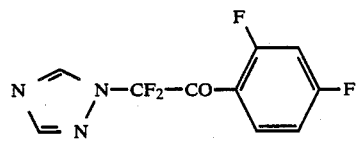

2-(1H-1,2,4-Triazol-1-yl)-2,2',4'-trifluoroacetophenoce (160 mg) was treated with ether-washed sodium hydride (25 mg) in dry tetrahydrofuran (5 ml) to give an orange solution. This solution was exposed to an atmosphere of perchloryl fluoride, when rapid uptake of this chemical occurred to give a pale yellow suspension. The tetrahydrofuran was removed under reduced pressure, the residue was partitioned between water (10 ml) and ethyl acetate (10 ml), the organic layer dried (MgSO$_4$) and evaporated to give the title compound as an oil, 127 mg.

N.m.r. (CDCl$_3$) δ=6.95(m),2H; 8.0(s),1H; 8.2(m),1H; 8.69(s),1H.

(ii)
1,3-Bis(1H-1,2,4-triazol-1-yl)-2-(2,4-difluorophenyl)-1,1-difluoropropan-2-ol

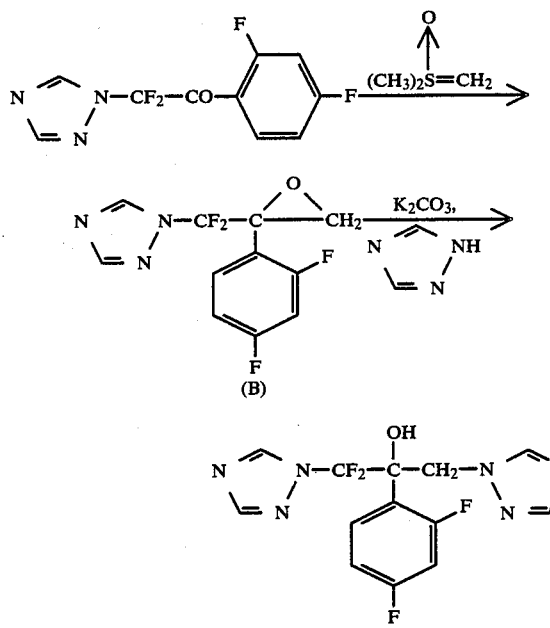

PROCEDURE (A)

Dimethyloxosulphonium methylide was prepared from trimethylsulphoxonium iodide (0.44 g) and sodium hydride (0.12 g of a 50% suspension in oil) in dry dimethylsulphoxide (10 ml) at 50°. Dry tetrahydrofuran (10 ml) was added, and the mixture was cooled to −40°. Crude 2-(1H-1,2,4-triazol-1-yl)-2,2,2',4'-tetrafluoroacetophenone (0.52 g) was added in dry tetrahydrofuran (5 ml). The mixture was stirred at −40° for 10 minutes, then allowed to rise in temperature to −10° over 15 minutes, then poured onto ice 100 g), and extracted with ethyl acetate (2×50 ml). The combined ethyl acetate extracts were washed with brine (2×10 ml), dried (MgSO$_4$) and evaporated to give the oxirane (B) as an oil, 240 mg. This oil was heated in dimethylformamide (5 ml) at 50° for three hours with potassium carbonate (200 mg) and 1,2,4-triazole (200 mg). The reaction mixture was then allowed to cool, poured into water (30 ml), and extracted with ethyl acetate (3×15 ml). The combined organic extracts were washed with brine (2×5 ml), dried (MgSO$_4$) and evaporated to an oil, 235 mg.

Flash chromatography of this oil on silica, eluting with methylene chloride containing isopropanol (10% v/v) and 0.880 (S.G.) ammonium hydroxide (1% v/v), gave a material of Rf 0.3 (in the same solvent system), 53 mg, which solidified on trituration with ether. Crystallisation of this solid from cyclohexane/ethyl acetate gave colourless crystals of the title compound, m.p. 132°–133°.

| Analysis % | |
|---|---|
| Required for C$_{13}$H$_{10}$F$_4$N$_6$O: | C,45.7; H,2.9; N,24.6; |
| Found: | C,45.6; H,3.0; N,24.3 |

N.m.r. (CDCl$_3$) δ=4.77(d), 1H, J=14 Hz; 5.39(d),1H,J=14 Hz; 6.1(6s),1H; 6.75(m),2H;7.44(dd),1H,J=14 Hz,7 Hz; 7.73(s),1E; 7.82(s),1H; 7.10(s),1H;8.32(s),1H.

m/e 343 (M+1).

PROCEDURE (B)

This is an alternative to route (a). In this route the oxirane (B) is not isolated.

Dimethyloxosulphonium methylide was prepared from trimethylsulphoxonium iodide (1.2 g) and sodium hydride (0.3 g of a 50% dispersion in oil) in dimethyl sulphoxide (20 ml). Dry tetrahydrofuran (30 mJ) was then added and the mixture was cooled to −35°. 2-(1H-1,2,4-Triazol-1-yl)-2,2,2',4'-tetrafluoroacetophenone (1.3 g) was added in tetrahydrofuran (5 ml) and the mixture was stirred at −30≧ for 15 minutes, allowed to rise to −10° over 15 minutes, stirred for 30 minutes at −10°, and then allowed to rise to 10° over 15 minutes. At this stage 1,2,4-triazole (1.0 g) and anhydrous potassium carbonate (1.0 g) were added and the mixture was heated to 70° for 3 hours, then stirred overnight at room temperature. The reaction mixture was then poured into water (150 ml) and extracted with ethyl acetate (3×100 ml). The combined organic extracts were dried (MgSO$_4$), evaporated to an oil (1.6 g), and flash chromatographed on silica, eluting with methylene chloride/isopropanol/ammonia (0.880) (90:10:1 by volume) to give, on evaporation of the appropriate fractions, a crystalline solid, 447 mg. Re-crystallisation of this solid from cyclohexane/ethyl acetate gave colourless crystals, m.p. 132°–133°, identical to the product of Procedure (a).

EXAMPLE 8

1,3-Bis(1H-1,2,4-triazol-1-yl)-2-(2,4-dichlorophenyl)-1,1-difluoropropan-2-ol, m.p. 155°–156°, was prepared similarly to the process of Example 7(b) from appropriate starting materials.

| Analysis % | |
|---|---|
| Found: | C,41.8; H,2.7; N,22.5; |
| Calculated for C$_{13}$H$_{10}$Cl$_2$F$_2$N$_6$O: | C,41.6; H,2.7; N,22.4. |

The starting ketone, 2',4'-dichloro-2,2-difluoro-2-(1H-1,2,4-triazol-1-yl)acetophenone, was prepared similarly to Example 7 part (i). It was an oil. N.m.r. (CDCl$_3$) δ=7.3 (m), 3H; 7.55 (s), 1H; 7.8 (s), 1H.

EXAMPLE 9

(i)
2-(2,4-Difluorophenyl)-3-fluoro-3-(1H-1,2,4-triazol-1-yl)-prop-1-ene

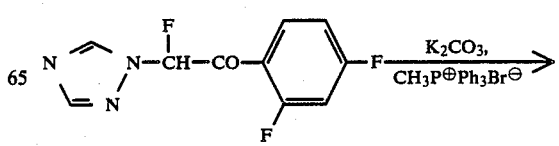

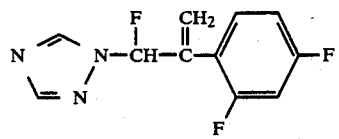

2-(1H-1,2,4-Triazol-1-yl)-2,2',4'-trifluoroacetophenone (10 g), anhydrous potassium carbonate (7.3 g), and methyltriphenylphosphonium bromide (15.5 g) were heated under reflux for 16 hours in 1,4-dioxan (250 ml), to which water (1.0 g) had been added.

A further amount of methyltriphenylphosphonium bromide (0.74 g) was then added, and heating was continued for a further 1 hour, when t.l.c. (silica, eluting with ether) showed that no starting material remained. The dioxan was then removed under reduced pressure, and the dark brown residue was triturated with ether (150 ml), when a precipitate of inorganic material and triphenylphosphine oxide formed. The ether solution was decanted from the precipitate, the precipitate was washed with ether (100 ml) and the washings were added to the decanted ether solution. The combined ether solutions were evaporated to a dark brown oil, 20.0 g.

This oil was chromatographed on silica (250 g), eluting with ether. The fractions containing product (as judged by t.l.c.) were combined and evaporated to yield the title compound as an amber oil, 9.6 g.

N.m.r (CDCl$_3$): δ=5.78 (dd), 1H, J4 Hz, 2 Hz; 6.03 (d), 1H, J2 Hz; 7.0, (m) 4H; 7.9 (s) 1H; 8.25 (s) 1H.

(ii)
1,3-Bis(1H-1,2,4-triazol-1-yl)-2-(2,4-difluorophenyl)-1-fluoropropan-2-ol

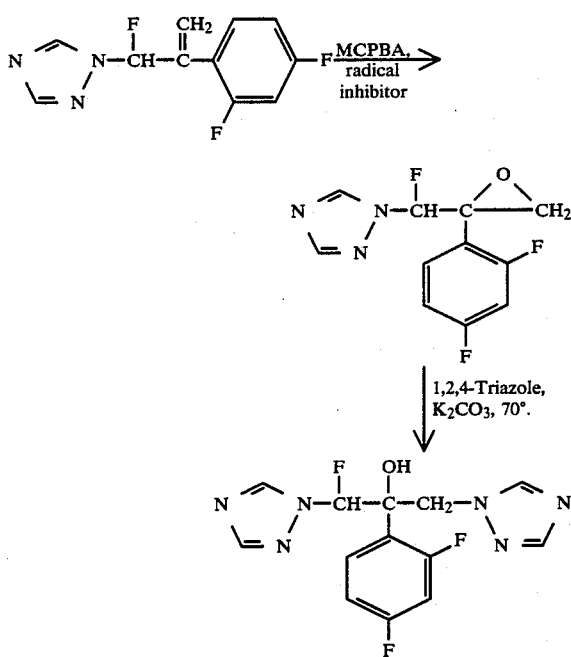

2-(2,4-Difluorophenyl)-3-fluoro-3-(1H-1,2,4-triazol-1-yl)prop-1-ene (5.0 g), m-chloroperbenzoic acid (10.8 g) (MCPBA) and a radical inhibitor, 3,3'-di-t-butyl-4,4'-dihydroxy-5,5'-dimethyldiphenylsulphide (0.22 g), were heated under reflux in 1,2-dichloroethane (75 ml) for 3 hours. The n.m.r. spectrum of an aliquot indicated that some starting material remained, so a further quantity of m-chloroperbenzoic acid (3.5 g) was added, and the reaction mixture was heated for a further 1 hour. After cooling and filtering to remove m-chlorobenzoic acid, the reaction mixture was diluted with methylene chloride (150 ml), washed with 10% sodium bisulphite solution (2×50 ml), and then with saturated sodium bicarbonate solution (2×100 ml). The organic layer was then washed with saturated sodium chloride solution (2×50 ml.), dried (MgSO$_4$) and evaporated to a yellow oil, 7.7 g.

The n.m.r. of this oil showed it to contain the epoxide as a mixture of two diastereomeric pairs in a ratio of 3:2, together with other organic residue. The total yield of epoxide was estimated to ba about 50%. This crude reaction product was reacted with 1,2,4-triazole (7.5 g) and potassium carbonate (7.5 g) in dimethylformamide (100 ml) at 70° overnight. The reaction mixture was then cooled, diluted to 300 ml. with water, and extracted with ethyl acetate (3×100 ml.). The organic extract was washed with saturated sodium chloride solution (2×50 ml), dried (MgSO$_4$), and evaporated to a dark brown oil, 4.8 g. This oil was chromatographed on silica (200 g), eluting first with ethyl acetate, 1.5 liters, and then with ethyl acetate containing 5% isopropanol gradually increasing to 20% isopropanol (by volume). The later fractions contained the desired product as judged by t.l.c. and were evaporated to a white solid, 1.4 g., which was triturated with ether to give a white solid, 1.15 g., m.p. 138°–140°: This material was confirmed spectroscopically to be identical to the second diastereoisomeric pair isolated in Example 2.

The following preparations illustrate the preparation of certain starting materials. All temperatures are in °C.:

PREPARATION 1

(i) 2,2',4'-Trifluoroacetophenone

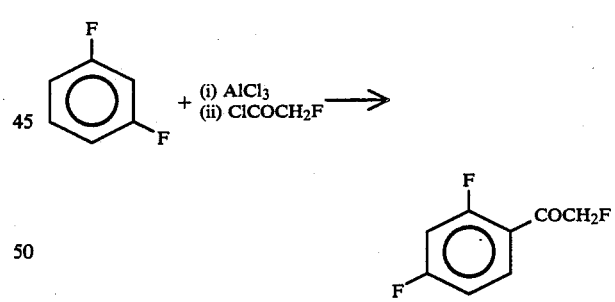

1,3-Difluorobenzene (2.02 g; 17.7 mM) and anhydrous aluminium chloride (2.60 g; 19.47 mM) were stirred together under dry nitrogen at room temperature. A solution of fluoroacetyl chloride (1,71 g; 17.7 mM) in anhydrous methylene chloride (2 ml) was added over 30 minutes. The mixture was then warmed at about 50° for 3 hours. On cooling methylene chloride (40 ml) was added and the mixture was poured onto ice. The methylene chloride layer was separated, dried over magnesium sulphate and evaporated to give a white solid. This material was chromatographed on a column of silica eluting with a mixture of hexane/methylene chloride (65:35 by volume). The product-containing fractions were collected. The title compound crystallised on evaporation of these fractions and was dried in a vacuum desiccator to a colourless crystalline solid (1.12 g; 36% yield), melting point 57°–8°.

| Analysis % | |
|---|---|
| Found: | C,55.0; H,2.8; |
| Required for $C_8H_5F_3O$: | C,55.2; H,2.9. |

(ii) 2,2',4'-Trifluoro-2-chloroacetophenone

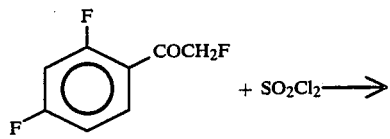

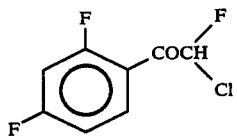

A solution of 2,2',4'-trifluoroacetophenone (1.60 g; 9.2 mM) in sulphuryl chloride (4 ml) was heated at 75° for 18 hours. The mixture was then cooled and iced-water (40 ml) was added. The product was extracted into ether (80 ml), which was washed with water and aqueous sodium bicarbonate solution, and then dried over magnesium sulphate. Evaporation yielded the desired product as a colourless, intensely lachrymatory liquid (2.0 g; 100%).

This liquid had N.M.R. and I.R. spectra consistent with the desired structure and was used directly in the next stage.

[N.m.r. ($CDCl_3$): δ = 8.05(m,1H); 6.95(m,2H); 6.87(d,1H,J=51)

I.R. (KBr), $-\underset{\underset{O}{\|}}{C}-$ at 1710 cm$^{-1}$.]

(iii)
2-(1H-1,2,4-Triazol-1-yl)-2,2',4'-trifluoroacetophenone

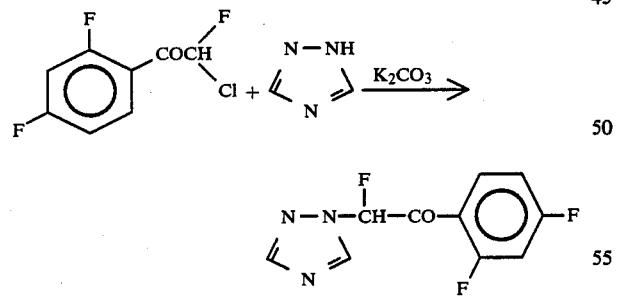

A mixture of 1,2,4-triazole (1.25 g); 18 mM) and anhydrous potassium carbonate (2.0 g; 14.5 mM) in anhydrous tetrahydrofuran (20 ml) was stirred at the reflux temperature. A solution of 2,2'4'-trifluoro-2-chloroacetophenone (1.5 g; 7.19 mM) in tetrahydrofuran (10 ml) was then added over a ten minute period. The mixture was refluxed for 2 hours and then stood overnight at room temperature. Water (50 ml) was added and the mixture was extracted with methylene chloride (2×100 ml). The combined organic extracts were dried over magnesium sulphate and evaporated to yield a gum. Chromatography on a column of silica, eluting with a mixture of ethylacetate/hexane/diethylamine (ratio 70:30:3 by volume) yielded, after evaporation of appropriate fractions, the desired product as a gum, (130 mg; 7.5%). The n.m.r. was consistent with the desired structure.

The compound was characterised as the methanesulphonic acid salt, m.p. 158°–160° prepared by mixing a solution of the free base in ether/acetone with a solution of the acid in ether/acetone and collecting the precipitated salt.

| Analysis % | |
|---|---|
| Found: | C,39.1; H,3.0; N,12.4; |
| Calculated for $C_{10}H_6F_3N_3O.CH_4O_3S$: | C,39.2; H,3.0; N,12.5. |

PREPARATION 2

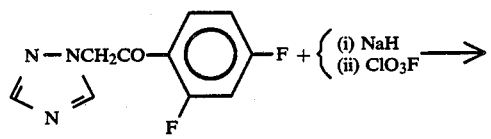

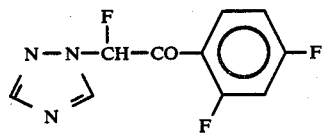

Sodium hydride (285 mg of a 50% dispersion in oil; 5.94 mM of sodium hydride) was washed with ether and dried under nitrogen. Anhydrous tetrahydrofuran was added (15 ml), followed by 2',4'-difluoro-2-(1H-1,2,4-triazol-1-yl)-acetophenone (1.115 g; 5 mM) (see U K. patent application publication No. 2099818A) in portions over a 5 minute period. The resultant brown solution was stirred under an atmosphere of perchloryl fluoride until the theoretical amount had been absorbed. The pale yellow suspension was evaporated and partitioned between water (25 ml) and ethyl acetate (50 ml). The ethyl acetate phase was separated, washed with water, dried over magnesium sulphate and evaporated to give an oil which crystallised (1.21 g).

The product was confirmed by n.m.r. and t.l.c. to be the same as the product of Preparation 1 (iii), free base form, in about 80% purity.

PREPARATIONS 3-6

The following ketone intermediates were prepared similarly to the process of Preparation 2 from the appropriate acetophenone or propiophenone, sodium hydride and perchloryl fluoride:

$$N \overset{\diagup N}{\underset{\diagdown N}{=}} N - \underset{R^1}{\overset{F}{\underset{|}{C}}} - CO - R$$

| Preparation No. | R | $R^1$ | m.p. (°C.) | Analysis % (or n.m.r.) (Theoretical in brackets) C H N |
|---|---|---|---|---|
| 3 | 4-F-C6H4 | H | 98–100 | N.m.r. (CDCl3): δ = 7.2 (m), 2H; 7.3 (d), 1H, J 48Hz; 8.1 (m), 3H; 8.5 (s), 1H. |
| 4 | 4-Cl-C6H4 | H | 137–8 | 50.3  3.0  17.5 (50.2  2.9  17.6) |
| 5 | 2,4-Cl2-C6H3 | H | 64–66 | 43.9  2.2  15.4 (43.9  2.2  15.4) |
| 6 | 2,4-F2-C6H3 | CH3 | oil | N.m.r. (CDCl3): δ = 2.25 (d), 3H, J 19Hz; 6.9 (m), 2H; 7.8 (m) 1H; 8.0 (s), 1H; 8.45 (s), 1H |

The starting acetophenones and propiophenone were prepared analogously to the procedure described in GB No. 2099818A for the preparation of 2',4'-difluoro-2-(1H-1,2,4-triazol-1-yl)acetophenone.

ACTIVITY DATA $PD_{50}$ values (mg/kg.) in mice infected with *Candida albicans* obtained for the compounds of the Examples and related compounds by the test procedure described in the text are as follows:

TABLE I

Oral $PD_{50}$ values in mice infected with *Candida albicans* Y0102 for compounds (A)

$$T-CH-\underset{R}{\overset{X}{\underset{|}{C}}}-\underset{R^2}{\overset{R^1}{\underset{|}{C}}}-Y \quad (A)$$
$$\qquad \overset{|}{R^3}$$

(T = 1H-1,2,4-triazol-1-yl)

| Product of Example | R | Y | X | $R^1$ | $R^2$ | $R^3$ | $PD_{50}$ (mg/kg) |
|---|---|---|---|---|---|---|---|
| 2 | 2,4-F2C6H3 | T (a) | OH | H | F | H | 0.29 |
| 2 | 2,4-F2C6H3 | T (b) | OH | H | F | H | 0.05 |
| 3 | 4-ClC6H4 | T | OH | H | F | H | 0.2 |
| 4 | 4-FC6H4 | T | OH | H | F | H | <1 |
| 5 | 2,4-Cl2C6H3 | T (c) | OH | H | F | H | 0.13 |
| 5 | 2,4-Cl2C6H3 | T (d) | OH | H | F | H | 0.49 |
| 6 | 2,4-F2C6H3 | T | OH | CH3 | F | H | 0.32 |
| 7 | 2,4-F2C6H3 | T | OH | F | F | H | 0.06 |
| 8 | 2,4-Cl2C6H3 | T | OH | F | F | H | 0.2 |

TABLE I-continued

Oral $PD_{50}$ values in mice infected with *Candida albicans* Y0102 for compounds (A)

$$T-CH-\underset{R}{\overset{X}{\underset{|}{C}}}-\underset{R^2}{\overset{R^1}{\underset{|}{C}}}-Y \quad (A)$$
$$\qquad \overset{|}{R^3}$$

(T = 1H-1,2,4-triazol-1-yl)

| Product of Example | R | Y | X | $R^1$ | $R^2$ | $R^3$ | $PD_{50}$ (mg/kg) |
|---|---|---|---|---|---|---|---|
|  | 2,4-F2C6H3 | T (e) | OH | H | H | H | 0.04 |
|  | 2,4-F2C6H3 |  | Cl | H | H | H | 0.9 |
|  | 2,4-F2C6H3 |  | Br | H | H | H | 0.3 |
|  | 2,4-F2C6H3 |  | F | H | H | H | >5 |

(a) diastereomeric pair 1
(b) diastereomeric pair 2
(c) mixture of diastereomers
(d) separated diastereomer
(e) fluconazole

TABLE II

Increase in mean survival times (MST's) against mice infected with *A. flavus* for the compounds (B)

$$N\overset{\diagup N}{\underset{\diagdown N}{=}}N-CH_2-\underset{R}{\overset{OH}{\underset{|}{C}}}-\underset{R^2}{\overset{R^1}{\underset{|}{C}}}-N\overset{\diagup N}{\underset{\diagdown N}{=}} \quad (B)$$

| Compound | R | $R^1$ | $R^2$ | Increase in MST (days) |
|---|---|---|---|---|
| 1 (a) | 2,4-Difluorophenyl | H | F | 14.6 |
| 2 | " | F | F | ≥19 |
| 3 (b) | " | CH3 | F | ≥15.7 |
| 4 (c) | " | H | H | 4.8 |
| 5 | 5-Chloropyrid-2-yl | H | H | 3.0 |

(a) most active diastereomer of the product of Example 2
(b) mixture of diastereomers
(c) generically known as fluconazole Using the procedure described herein for determining activity against aspergillosis in mice and *A. fumigatus* as the causative organism, it was found that at a dose level of 12.5 mg/kg, fluconazole gave a MST of ≥11 days and the most active diastereomer of the product of Example 2 gave a MST of ≥23 days.

Expression of the MST values reported above for fluconazole and for the most active diastereomers of the product of Example 2 as $PD_{50}$ values demonstrates the beneficial and unexpected effect of placing a fluoro substituent on a carbon adjacent to a triazolyl ring.

| Compound | $PD_{50}$ (mg/kg) | |
|---|---|---|
|  | *A. fumigatus* | *A. flavus* |
| fluconazole | 13.4 | 3.2 |
| most active diastereomer of Ex. 2 | 3.6 | 0.3 |

We claim:
1. A triazole of the formula

$$N\overset{\diagup N}{\underset{\diagdown N}{=}}N-CH_2-\underset{R}{\overset{OH}{\underset{|}{C}}}-\underset{F}{\overset{R^1}{\underset{|}{C}}}-N\overset{\diagup N}{\underset{\diagdown N}{=}} \quad (I)$$

where R is 2,4-difluorophenyl; $R^1$ is H, CH3 or F; and a pharmaceutically and agriculturally acceptable salt thereof.

2. A compound according to claim 1 wherein $R^1$ is H or F.

3. The compound according to claim 1 wherein $R^1$ is H.

4. A composition comprising an antifungally effective amount of a compound of claim 1, or a pharmaceutically or an agriculturally acceptable salt thereof, and a pharmaceutically or an agriculturally acceptable carrier.

5. A method of treating a fungal infection in an animal which comprises treating said animal with an antifungally effective amount of a compound of claim 1.

* * * * *